(12) United States Patent
Park et al.

(10) Patent No.: US 8,317,826 B2
(45) Date of Patent: Nov. 27, 2012

(54) ABSORBABLE BULKY MULTI-FILAMENT DRAW TEXTURED YARN, MANUFACTURING METHOD THEREOF AND MEDICAL USE USING THEM

(75) Inventors: Young Hwan Park, Anyang-si (KR); Jung Nam Im, Gunpo-si (KR); Jae Hoon Ko, Seoul (KR); Kyoung Woo Lee, Incheon (KR); Yong Woo Cho, Seoul (KR)

(73) Assignee: Korea Institute of Industrial Technology, Chungcheongnam-do (KR)

( * ) Notice: Subject to any disclaimer, the term of this patent is extended or adjusted under 35 U.S.C. 154(b) by 424 days.

(21) Appl. No.: 12/587,461

(22) Filed: Oct. 7, 2009

(65) Prior Publication Data

US 2010/0087856 A1 Apr. 8, 2010

(30) Foreign Application Priority Data

Oct. 7, 2008 (KR) .................. 10-2008-0098342

(51) Int. Cl.
*A61B 17/04* (2006.01)
*A61F 13/00* (2006.01)
(52) U.S. Cl. ....................... 606/230; 424/443
(58) Field of Classification Search .......... 606/228–231, 606/224; 424/422–424, 426, 443, 444
See application file for complete search history.

(56) References Cited

U.S. PATENT DOCUMENTS

| | | | |
|---|---|---|---|
| 3,636,956 A * | 1/1972 | Schneider | 606/224 |
| 6,743,505 B2 | 6/2004 | Antal et al. | |
| 7,192,604 B2 * | 3/2007 | Brown et al. | 424/422 |
| 7,207,962 B2 | 4/2007 | Anand et al. | |
| 7,445,793 B2 | 11/2008 | Niwa et al. | |

FOREIGN PATENT DOCUMENTS

KR 638736 10/2006
WO WO 2006/116000 11/2006

OTHER PUBLICATIONS

A. G. Mikos, et al.; *Polymer*; 35, 1068 (1994).
L. D. Harris, et al.; *Journal of Biomedical Materials Research*; 42, 396 (1998).
K. T. Paige, et al., *Tissue Engineering*; 1, 97 (1995).
C. Schugens, et al.; *Journal of Biomedical Materials Research*; 30, 449 (1996).
K. T. Paige, et al.; *Tissue Engineering*; 1, 97 (1995).

* cited by examiner

*Primary Examiner* — Julian Woo
(74) *Attorney, Agent, or Firm* — D. Peter Hochberg; Sean F. Mellin; Daniel J. Smola (57) ABSTRACT

An absorbable multifilament draw-textured yarn having a bulky structure, and a manufacturing method and medical use thereof The absorbable multifilament draw-textured yarn is obtained by draw-texturing a multifilament made of an absorbable polymer and has bulkiness and a superior soft touch, which are the characteristics of draw-textured yarns. As a result of partially imparting a bulkiness of 150-1000% to the multifilament draw-textured yarn, it is possible to culture cells in the bulky structure, and the multifilament draw-textured yarn is suitable for cell delivery or drug delivery.

9 Claims, 5 Drawing Sheets

ABSORBABLE BULKY MULTI-FILAMENT DRAW TEXTURED YARN, MANUFACTURING METHOD THEREOF AND MEDICAL USE USING THEM

CROSS-REFERENCE TO RELATED APPLICATIONS

This application claims foreign priority to Korean Patent Application Serial No. 10-2008-98342, filed on Oct. 7, 2008, the content of which is incorporated by reference herein in its entirety.

BACKGROUND OF THE INVENTION

1. Field of the Invention

The present invention relates to an absorbable bulky multifilament draw-textured yarn, and a manufacturing method and medical use thereof, and more particularly to an absorbable multifilament draw-textured yarn wherein a bulky structure is partially imparted to a draw-textured yarn (hereinafter referred to as "DTY"), such that the absorbable multifilament draw-textured yarn easily performs cell culture, cell delivery or drug delivery, and a manufacturing method and medical use thereof.

2. Description of the Prior Art

One typical tissue engineering technique comprises: collecting a required tissue from a patient body; isolating a cell from the removed tissue; proliferating the isolated cell; seeding the cell in an absorbable porous polymer scaffold; culturing the cell in vitro for a predetermined period; and transplanting the obtained hybrid-type cell/polymer structure into the human body. After the transplantation is achieved, oxygen and nutrients are provided to the transplanted cells in absorbable porous polymer due to the diffusion of body fluids until a blood vessel is newly formed. When the blood vessel is formed to which blood is supplied, the cells proliferate and differentiate to form a new tissue and organ. During the formation of new tissue and organ, the polymer scaffolds are degraded and then metabolized in the body.

Accordingly, in the field of tissue engineering, it is important to prepare an absorbable polymer scaffold that is similar to the body tissue.

In order to be used as a raw material for the polymer scaffolds, the material should have sufficient mechanical strength, such that it can properly serve as a scaffold so that tissue cells can adhere to the surface of the material and form a tissue in a three-dimensional structure. It should also serve as a middle barrier, which is positioned between a transplanted cell and a host cell. For this purpose, it should be non-toxic and biocompatible such that neither blood coagulation nor inflammatory reaction occurs after the transplantation.

In addition, such material should be absorbable so that the transplanted cell properly functions as a new tissue in the body, it is completely absorbed by the body within a desired period of time.

Typical examples of absorbable polymers which are currently generally used as raw materials for scaffolds include natural polymers, such as collagen, chitosan, gelatin, hyaluronic acid or alginic acid, and synthetic polymers, such as polylactic acid (PLA), polyglycolic acid (PGA) or poly-$\epsilon$-caprolactone (PCL), or copolymers thereof.

Cell culture scaffolds prepared using such absorbable natural polymers or synthetic polymers must have high porosity and high strength so as to facilitate cell injection and proliferation.

Recently, in order to prepare a scaffold structure satisfying such requirements, researchers have made various attempts to prepare a polymer having a porous structure through various techniques. Typical examples of such techniques include: a solvent-casting and particulate-leaching technique (A. G. Mikos, etc. Polymer, 35, 1068, 1994), wherein single crystal NaCl is mixed, dried and dissolved in water; a gas foaming technique (L. D. Harris, etc., Journal of Biomedical Materials Research, 42, 396, 1998), wherein a polymer is inflated by using $CO_2$ gas; a fiber extrusion and fabric foaming process (K. T. Paige, etc. Tissue Engineering, 1, 97, 1995), wherein a polymer fiber is formed into a nonwoven fabric to make a polymer mesh; a thermally induced phase separation technique (C. Schugens, etc., Journal of Biomedical Materials Research, 30, 449, 1996), wherein a solvent contained in a polymer solution is immersed in a nonsolvent to produce porosity; and an electrospinning technique (Korean Patent Registration No. 638736) wherein a nanofiber yarn is electrospun to form foam cells in the strand of the nanofiber yarn so as to increase the porosity of a three-dimensional cell scaffold.

In the case of the solvent-casting and particulate-leaching technique, the preparation process is easy, but there is a problem in that the pore on the surface layer is blocked, because the surface is rough and the salt remains on the surface. In the case of the gas foaming method, pores which are weakly interconnected are formed, and thus there is a limitation in terms of the injection of cells. In addition, in the case of the fiber extrusion and fabric foaming process of forming a polymer fiber into a nonwoven fabric to make a polymer mesh, a relatively high porosity can be achieved and the surface area can be optimized, but low strength is still pointed out as a problem.

Meanwhile, in the thermally induced phase separation technique, it is easy to control the size of pores, but it is difficult to apply the separation technique in practice due to the formation of pores having a relatively small size. In addition, in the electrospinning technique, it is not easy to achieve satisfactory porosity, thus making cell injection difficult.

Accordingly, with the conventional methods, it is not easy to control the pore size of the scaffold. Furthermore, the surface area and porosity of the resultant polymer scaffolds are comparatively low and the open structures are not formed well. In addition, they are disadvantageous in that there are occurrences of closed pores on the surface of the scaffolds, the process is comparatively complicated, the gas or toxic substance maybe secreted during the preparation of scaffolds, and salt remains in the scaffolds.

Accordingly, the present inventors have made efforts to solve the problems occurring in the prior art and, as a result, have prepared an multifilament yarn of less than 30 μm in diameter using a conventional absorbable polymer for medical use, and have prepared a draw-textured yarn from the multifilament yarn so as to impart bulkiness and a soft touch. Furthermore, the present inventors have found that, when bulkiness is partially imparted to the draw-textured yarn, the draw-textured yarn can easily perform cell culture, cell delivery or drug delivery during a surgical operation so as to maximize the convenience of surgery, thereby completing the present invention.

SUMMARY OF THE PRESENT INVENTION

It is an object of the present invention to provide an absorbable multifilament draw-textured yarn wherein a bulky structure is imparted to a draw-textured yarn (DTY) made of an absorbable polymer.

Another object of the present invention is to provide a method for manufacturing the absorbable multifilament draw-textured yarn.

Still another object of the present invention is to provide the medical use of an absorbable multifilament draw-textured yarn which partially has a bulky structure.

To achieve the above objects, the present invention provides an absorbable multifilament draw-textured yarn wherein a bulky structure is imparted to a draw-textured yarn made of an absorbable polymer.

As used herein, the term "bulky structure" refers to a structure in which pores greater than 1 µm are present between fibers, and the term "bulkiness" refers to the diameter ratio of a portion having a bulky structure relative to a portion having no bulky structure. The bulky structure of the present invention has a bulkiness of 150-1000%, and preferably 200-600%. Also, the absorbable multifilament draw-textured yarn of the present invention has pores of 1-150 µm in the bulky structure, such that it is suitable for cell delivery, cell proliferation or drug delivery.

In the present invention, the absorbable polymer which is used as a raw material for the draw-textured yarn (DTY) is selected from the group consisting of homopolymer and copolymer of glycolide, glycolic acid, lactide, lactic acid, dioxanone, trimethylene carbonate and ethylene glycol. Alternatively, an absorbable natural polymer selected from the group consisting of collagen, cellulose oxide, chitosan, gelatin, fibrin, hyaluronic acid and alginate can be also used.

The present invention also provides a method for manufacturing an absorbable multifilament draw-textured yarn, the method comprising the steps of: spinning an absorbable polymer to prepare a multifilament yarn; plying the multifilament yarns while draw-texturing the multifilament yarns to prepare a multifilament draw-textured yarn; drawing or stretching the multifilament draw-textured yarn to impart a bulky structure to the draw-textured yarn; and twisting or braiding the multifilament draw-textured yarn having the bulky structure formed therein.

The manufacturing method of the present invention may additionally comprise a step of subjecting a portion of the twisted or braided multifilament draw-textured yarn to a coating process.

The multifilament yarn comprises plurality of filaments which have the diameter of 5-30 µm, and the plied multifilament yarn diameter of 40-1000 µm.

In the manufacturing method of the present invention, the multifilament draw-textured yarn having the bulky structure is drawn or stretched so as to have a bulkiness of 150-1000%, and the absorbable multifilament draw-textured yarn partially having the bulky structure is used to provide a cell culture scaffold.

Furthermore, the present invention provides an absorbable multifilament suture comprising an absorbable multifilament draw-texture yarn which partially has a bulky structure in a draw-textured yarn made of an absorbable polymer. Moreover, the suture can be manufactured by coupling a surgical needle to the absorbable multifilament draw-textured yarn, followed by sterile packaging.

According to the present invention, an absorbable multifilament draw-textured yarn suitable for medical use can be provided by partially imparting a bulkiness of 150-1000% to a draw-textured yarn made of an absorbable polymer.

The inventive absorbable multifilament draw-textured yarn which partially has a bulky structure is useful for cell or drug delivery, and thus is useful as a cell culture scaffold or a medical suture.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE PRESENT INVENTION

The present invention will be described in detail below.

Figure 1:
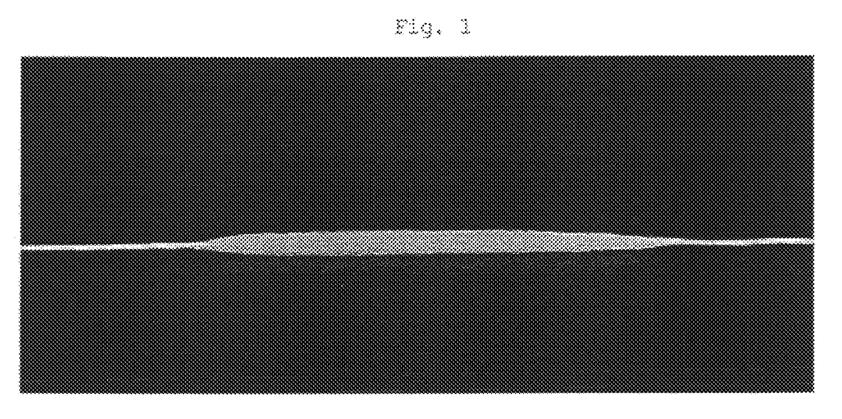
FIG. 1 is a photograph of the inventive absorbable multifilament draw-textured yarn having a bulky structure of the present invention.

The present invention provides an absorbable multifilament draw-textured yarn wherein a bulky structure is partially imparted to a draw-textured yarn (DTY) made of an absorbable polymer (see FIG. 1).

The draw-textured yarn is obtained by draw-texturing the multifilament made of an absorbable polymer and has bulkiness and a superior soft touch, which are the characteristics of draw-textured yarns. According to the present invention, a bulky structure is partially imparted to the multifilament draw-textured yarn, such that the draw-textured yarn is suitable for cell culture, cell delivery or drug delivery in medical applications.

As used herein, the term "bulky structure" refers to a structure in which pores greater than 1 µm are present between filaments. The bulky structure is formed by drawing or stretching the multifilament draw-texturing yarn made of the absorbable polymer. A bulkiness of 150-1000%, and preferably 200-600% is partially imparted to the absorbable multifilament draw-textured yarn through the twisting or braiding process.

Specifically, the multifilament draw-textured yarn of the present invention has a bulky structure including pores of 1-150 µm, and preferably 5-50 µm, and thus it is easy to form open structures between the filaments due to high porosity.

The bulkiness of the multifilament draw-textured yarn may be freely controlled depending on its intended use such as cell culture, cell delivery or drug delivery. If the bulkiness is less than 150%, the pores between the fibers will become smaller, so that cell proliferation in cell culture will become difficult, the amount of cell or drug that can be delivered into a living body will become smaller, and thus the utility as a scaffold for medical applications will be reduced. On the other hand, if the bulkiness exceeds 1000%, yarn breakage rate will be increased due to the weak durability of the absorbable polymer, and pores between fibers will become excessively larger, leading to a decrease in the ability to retain a cell or drug.

Figure 2:
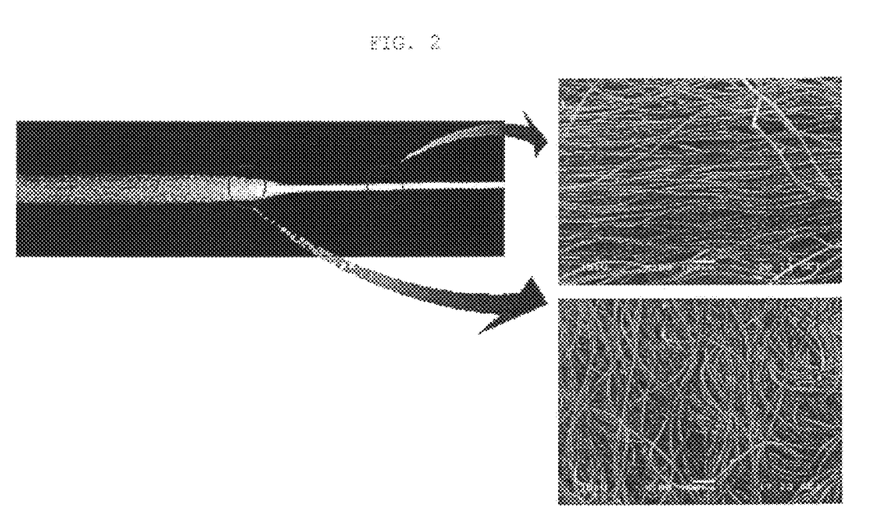
FIG. 2 is a scanning electron microscope image of the inventive absorbable multifilament draw-textured yarn having a bulky structure of the present invention.

FIG. 2 is a scanning electron microscope image of the absorbable bulky multifilament draw-textured yarn of the present invention. As shown therein, the absorbable multifilament draw-textured yarn has pores in the bulky structure. The degree of bulkiness or the size of pores is controllable depending upon drawing or stretching conditions during the manufacture of the draw-textured yarn.

It is to be understood that the pore size can be suitably controlled depending on the size of cell or drug selected. Specifically, the bulky structure of the multifilament draw-stretched yarn includes pores having a size of 1-150 μm, and preferably 5-50 μm. If the pore size is less than 1 μm, the pores between the fibers of the yarn will become smaller, so that cell proliferation in cell culture will become difficult, the amount of cell or drug that can be delivered into a living body will become smaller, and thus the utility as a scaffold for medical applications will be reduced. On the other hand, if the pore size exceeds 150 μm, the breakage rate of the yarn will be increased due to the weak durability of the absorbable polymer, and the pores between the filaments of the yarn will become excessively larger, leading to a decrease in the ability to retain a cell or drug.

Because it is preferable that a bulky multifilament draw-textured yarn for the purpose of cell culture or drug delivery is degraded and absorbed in vivo after achieving the purpose, it should be made of an absorbable polymer.

The absorbable polymer which is used in the present invention is not specifically limited as long as it is a biocompatible resin known in the art. Examples of the absorbable polymer include natural polymers and synthetic polymers. The absorbable synthetic polymer which is used in the present invention is selected from the group consisting of homopolymer and copolymer of glycolide, glycolic acid, lactide, lactic acid, caprolactone, dioxanone, trimethylene carbonate and ethylene glycol.

Also, examples of the absorbable natural polymer which can be used in the present invention include collagen, cellulose oxide, chitosan, gelatin, hyaluronic acid and alginate.

The present invention provides a method for manufacturing an absorbable multifilament draw-textured yarn wherein a bulky structure is partially imparted to a draw-textured yarn (DTY) made of an absorbable polymer.

More specifically, the manufacturing method of the present invention comprises the steps of:

(1) spinning an absorbable polymer to prepare a multifilament yarn;
(2) plying the multifilament yarns with each other while draw-texturing the yarns to prepare a multifilament draw-textured yarn;
(3) drawing or stretching the multifilament draw-textured yarn to impart a bulky structure to the textured yarn; and
(4) twisting or braiding the multifilament draw-textured yarn having the bulky structure therein to impart mechanical strength and dimensional stability.

Moreover, the manufacturing method of the present invention may additionally comprise a step (5) of performing coating on a portion of the multifilament draw-textured yarn imparted with dimensional stability by the twisting or braiding process.

In step (1) of the method, a synthetic absorbable polymer selected from the group consisting of homopolymer and copolymer of glycolide, glycolic acid, lactide, lactic acid, caprolactone, dioxanone, trimethylene carbonate and ethylene glycol, or an absorbable natural polymer selected from the group consisting of collagen, cellulose oxide, chitosan, gelatin, fibrin, hyaluronic acid and alginate is through a spinnerette to prepare an multifilament yarn having the diameter of 5-30 μm for single filament.

The absorbable multifilament yarn of step (1) is an multifilament yarn having the diameter not greater than 30 μm, while it has satisfactory properties of a tenacity of 2.0-9.0 g/d and an elongation of 20-80%. Thus, it can minimize the occurrence of yarn breakage in the subsequent draw-texturing process.

On the other hand, if the diameter of single filament in the inventive absorbable multifilament yarn is greater than 30 μm, the degradation rate of the yarn after cell culture, cell delivery or drug delivery can be slower, and the yarn will be stiff so the convenience of surgery will be reduced.

If the elongation of the multifilament yarn made of the absorbable polymer is less than 20%, the texturing workability of the yarn will be rapidly deteriorated. The higher the elongation of the yarn, the better the workability; however, if the elongation of the multifilament yarn is more than 80%, the workability of the yarn will be significantly deteriorated. Accordingly, the multifilament yarn which is used in the present invention preferably has an elongation of 25-40%. Also, if the tenacity of the multifilament yarn is less than 2.0 g/d, the texturing workability of the yarn will be deteriorated, and if it is more than 9.0 g/d, the soft touch of the draw-textured yarn will be reduced.

The diameter of the plied multifilament yarn obtained in step (2) may vary depending on the application field and intended use of the resultant yarn. If the resultant yarn is applied to medical sutures, the plied multifilament yarn will preferably have a diameter of 40-1000 μm, and more preferably 40-800 μm.

If the diameter of the plied yarn is less than 40 μm, yarn breakage will be likely to occur during the stretching/draw-twisting process and the efficiency of production of the bulky structure will be low, and the tenacity of the yarn will be low, leading to a decrease in the convenience of implantation. If the diameter is more than 1000 μm, it will be difficult to apply the yarn in vivo by a surgical operation using a conventional suturing technique, and the foreign body reaction of the polymer used in vivo will be increased.

Subsequently, the plied multifilament yarn made of the absorbable polymer is subjected to a draw-texturing process to prepare a multifilament draw-textured yarn. In order to ensure the texturing workability and the quality of the draw-textured yarn, the draw-texturing process is carried out at a linear velocity of 200-700 m/min, and preferably 250-400 m/min, at a drawing ratio of 1.01-1.8, and preferably 1.02-1.7.

Step (3) of the manufacturing method of the present invention is a step of stretching or drawing the multifilament draw-textured yarn prepared in step (2) to impart a bulky structure to the draw-textured yarn. In step (3), one process of imparting the bulky structure is carried out by winding the absorbable multifilament draw-textured yarn on a stretchable rack, and then stretching the wound yarn by 3-10%, and preferably 4-7%. If the stretch ratio is less than 3%, it will be difficult to make the bulky structure, and if it will exceed 10%, yarn breakage will be likely to occur.

Another process of imparting the bulky structure is carried out by a drawing method in a continuous process.

Step (4) of the manufacturing method of the present invention is a step of twisting or braiding the multifilament draw-textured yarn having the bulky structure formed in step (3).

The twisting or braiding process is carried out in order to improve the cohesion, mechanical properties and use convenience of the multifilament draw-textured yarn. After the process of imparting the bulky structure, the multifilament draw-stretched yarn is separated from the rack, and then twisted at 200 turns/meter or less in order to maintain the bulky structure while enhancing the cohesion of the yarn.

Meanwhile, if the absorbable multifilament draw-textured yarn having the bulky structure is used as a suture, a braiding process may be used instead of the twisting process. The braiding process is carried out in such a manner that the predetermined portion is not braided to retain partially bulky structure.

The absorbable multifilament draw-textured yarn of the present invention manufactured through the above-described steps has a bulky structure including pores of 1-150 μm in diameter, and preferably 5-50 μm in diameter. The size of pores in the bulky structure is easily controlled, and the bulky structure shows high porosity.

The manufacturing method of the present invention may additionally comprise, after step (4), a step (5) of subjecting a portion of the twisted or braided multifilament draw-textured yarn to a coating process to further enhance the dimensional stability of the yarn and to reduce tissue drag during the implantation.

By additionally imparting cohesion to only a portion of the bulky multifilament draw-textured yarn trough the twisting or braiding process and the coating process, a bulkiness of 150-1000%, and preferably 200-600% is partially imparted to the incoherent portion of the multifilament draw-textured yarn.

Specifically, in the coating process, a coating solution containing 1-10 wt % of an absorbable polymer resin in an organic solvent is applied to the twisted or braided multifilament draw-textured yarn by a conventional method such as dip coating or spray coating.

Herein, the absorbable polymer resin which is used in the coating solution to form a thin film layer on the yarn surface is selected from the group consisting of homopolymer and copolymer of glycolide, glycolic acid, lactide, caprolactone, dioxanone, trimethylene carbonate and ethylene glycol, or an absorbable natural polymer consisting of the group consisting of collagen, cellulose oxide, chitosan, gelatin, fibrin, hyaluronic acid and alginate. Preferably, either a copolymer of glycolide and lactide (30:70) or polycaprolactone is dissolved in ethylene acetate or methylene chloride and used as the coating resin.

Also, for the convenience of implantation, a softener such as calcium stearate may be added to the coating solution.

The present invention also provides a cell culture scaffold which allows a cell or body tissue to proliferate in the bulky structure of a multifilament draw-structured yarn wherein the bulky structure is partially imparted to a draw-textured yarn (DTY) made of an absorbable polymer.

The bulky structure of the absorbable multifilament draw-textured yarn which partially has the bulky structure includes pores of 1-150 μm, and preferably 5-50 μm, and thus shows high porosity. Accordingly, the closing of pores the scaffold can be avoided.

Figure 3:
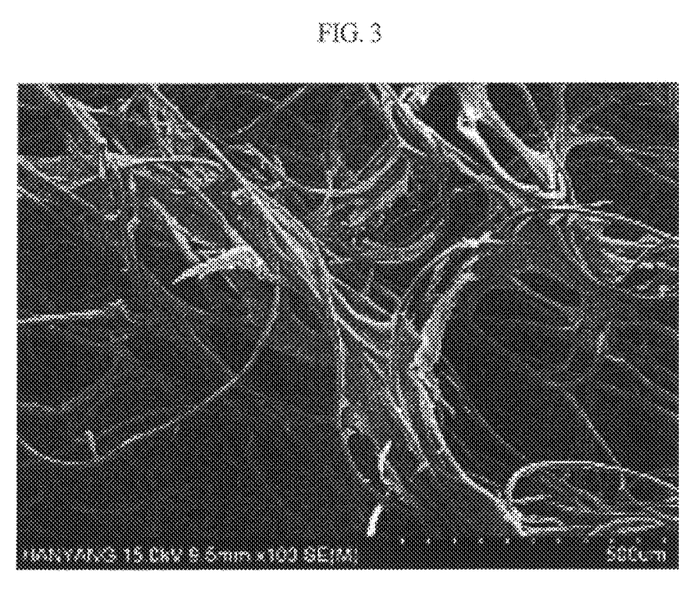
FIGS. 3 and 4 are, respectively 100× and 500× magnification image, respectively, which show the results of cell culture conduced using, as a scaffold, the inventive absorbable multifilament draw-textured yarn having a bulky structure of the present invention.
Figure 4:
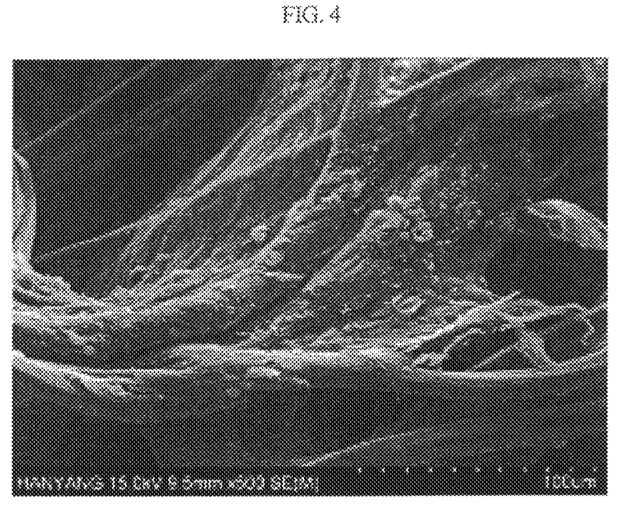

FIGS. 3 and 4 are, respectively, 100× or 500× magnification photographs showing the results obtained by culturing a cell (NIH 3T3 cell) for 3 days using the inventive absorbable multifilament draw-textured yarn as a scaffold.

The results shown in FIGS. 3 and 4 reveal that the absorbable multifilament draw-textured yarn which partially has the bulky structure in the draw-textured yarn made of the absorbable polymer can achieve cell culture in the bulky structure.

Furthermore, the present invention provides an absorbable multifilament suture comprising an absorbable multifilament draw-textured yarn wherein a bulky structure is partially imparted to a draw-textured yarn made of an absorbable polymer.

The absorbable multifilament suture of the present invention comprises an absorbable multifilament draw-textured yarn which partially has a bulky structure including pores of 1-150 μm, and preferably 5-50 μm, and which partially has a bulkiness of 150-1000%. Accordingly, when the absorbable multifilament suture of the present invention is used as a medical suture, it will be useful for cell culture, cell delivery or drug delivery, and thus can perform cell or drug delivery through a surgical operation, thereby maximizing the convenience of surgery.

Figure 5:
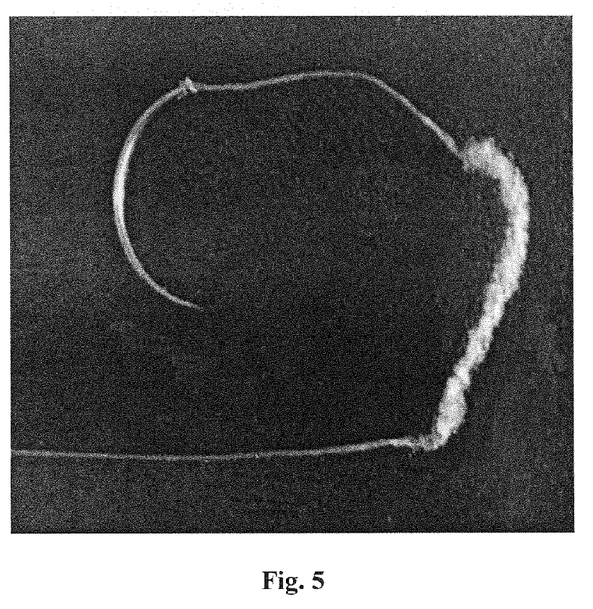
FIG. 5 is a photograph of the absorbable multfilament draw-textured yarn coupled with a surgical needle.

In addition, the suture of the present invention can be manufactured by coupling a surgical needle to the absorbable multifilament draw-textured yarn, followed by sterile packaging. FIG. 5 displays the surgical needle coupled to the absorbable multifilament draw-textured yarn.

Hereinafter, the present invention will be described in further detail with reference to examples. It is to be understood, however, that these examples are for illustrative purposes only and are not to be construed to limit the scope of the present invention.

EXAMPLE 1

Manufacturing the Multifilament Draw-Textured Yarn Having Bulky Structure 1

Poly(glycolide-co-lactide) consisting of glycolide and lactide at a weight ratio of 90:10 was melt-spinning by a conventional method to prepare a multifilament yarn consisting of 56 filaments each having a diameter of 15-17 μm. The multifilament yarn showed a tenacity of 7 g/d and an elongation of 40%.

Four bundle of multifilament yarn consisting of 56 filaments was plied using Murata 33H (belt type; belt angle 110°), while they were twisted on the first roller in the Z-direction, untwisted on the second roller, and then heat-set at 170° C., thus preparing a draw-textured yarn (DTY) consisting of 224 filaments. The draw-texturing process was performed at a draw ratio of 1.024 and a linear velocity of 250 m/min.

Then, the draw-textured yarn made of poly(glycolide-co-lactide) was wound on a stretchable rack, and then stretched by 4%, thus preparing a multifilament draw-textured yarn having a bulky structure.

The prepared bulky multifilament draw-textured yarn was separated from the rack, and then twisted at 80 turns/meter. The twisted multifilament draw-textured yarn was cut to a length of 45 cm, and the remainder other than about 5 cm of the central portion of the cut yarn was coated under tension such that the yarn was stretched by about 4%. Then, the coated yarn was dried for about 3 seconds in a convection oven at 40° C. The coating process was carried out using a coating solution containing 2 wt % of a copolymer of glycolide and lactide (30/70 w/w) in ethylene acetate.

EXAMPLE 2

Manufacturing the Multifilament Draw-Texturedyarn Having Bulky Structure 2

Polylactide was melt-spinning by a conventional method to prepare a multifilament yarn consisting of 72 filaments each having a diameter of 10-12 μm.

The multifilament yarn showed a tenacity of 3.2 g/d and elongation of 30%.

Four bundle of multifilament yarn consisting of 76 filaments was plied using Murata 33H (belt type; belt angle 100°), while they were twisted on the first roller in the Z-direction, untwisted on the second roller, and then heat-set at 115° C., thus preparing a draw-textured yarn (DTY) consisting of 288 filaments. The draw-texturing process was performed at a draw ratio of 1.63 and a linear velocity of 300 m/min.

Then, the draw-textured yarn made of polylactide was wound on a stretchable rack, and then stretched by 5%, thus preparing a multifilament draw-textured yarn having a bulky structure.

The prepared bulky multifilament draw-textured yarn was separated from the rack, and then twisted at 150 turns/meter. The twisted multifilament draw-textured yarn was cut to a length of 45 cm, and the remainder other than about 4 cm of the central portion of the cut yarn was coated under tension such that the yarn was stretched by about 5%. Then, the coated yarn was dried for about 3 seconds in a convection oven set at 40° C. The coating process was carried out using a coating solution containing 2 wt % of a copolymer of glycolide and lactide (30/70 w/w) in ethylene acetate.

EXAMPLE 3

Manufacturing the Multifilament Draw-Textured Yarn Having Bulky Structure 3

Poly(glycolide-co-lactide) consisting of glycolide and lactide at a weight ratio of 90:10 was melt-spinning by a conventional method to prepare a multifilament yarn consisting of 56 filaments each having a diameter of 15-17 μm. The multifilament yarn showed a tenacity of 7 g/d and an elongation of 40%.

The multifilament yarn was plied using Murata 33H (belt type; belt angle 110°), while they were twisted on the first roller in the Z-direction, untwisted on the second roller, and then heat-set at 170° C., thus preparing a draw-textured yarn (DTY) consisting of 224 filaments. The draw-texturing process was performed at a draw ratio of 1.024 and a linear velocity of 250 m/min.

Then, the draw-textured yarn made of poly(glycolide-co-lactide) was wound on a stretchable rack, and then stretched by 4%, thus preparing a multifilament draw-textured yarn having a bulky structure.

The prepared bulky multifilament draw-textured yarn was separated from the rack, plied two-fold, and then twisted at about 40 turns/meter, thus preparing a bulky multifilament draw-textured yarn consisting of 448 filaments.

The twisted multifilament draw-textured yarn was cut to a length of 70 cm, and the remainder other than about 5 cm of the central portion of the cut yarn was coated under tension such that the yarn was stretched by about 6%. Then, the coated yarn was dried for about 3 seconds in a convection oven set at 40° C. The coating process was carried out using a coating solution containing 2 wt % of polycaprolactone in methylene chloride.

As described above, according to the present invention, an absorbable multifilament draw-textured yarn suitable for medical use is provided by partially imparting a bulkiness of 150-1000% to a multifilament draw-textured yarn made of an absorbable polymer.

Moreover, through the method for manufacturing the absorbable multifilament draw-textured yarn, an multifilament yarn having a each diameter of 5-30 μm is provided using an absorbable polymer for medical use.

Furthermore, an absorbable multifilament draw-textured yarn having an ultra-bulky structure is provided. It is useful for cell delivery or drug delivery, and thus is useful as a cell culture scaffold or a medical suture.

In addition, the inventive absorbable multifilament draw-textured yarn having the bulky structure can perform cell or drug delivery during a surgical operation, and thus maximize the convenience of surgery.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. An absorbable multifilament draw-textured yarn comprising an absorbable polymer, wherein the absorbable multifilament draw-textured yarn partially has a bulkiness of, wherein said bulkiness is a diameter ratio of a portion of the absorbable multifilament draw-textured yarn having a bulky structure relative to a portion of the absorbable multifilament yarn having no bulky structure, said bulky structure being a structure of the absorbable multifilament draw-textured yarn having pores between said filaments, said pores being greater than 1 μm in diameter.

2. The absorbable multifilament draw-textured yarn according to claim 1, wherein a bulkiness of 200-600% is partially imparted to the absorbable multifilament draw-textured yarn.

3. The absorbable multifilament draw-textured yarn according to claim 1 comprising pores in the range of 1-150 μm in diameter.

4. A cell culture scaffold which allows a cell or body tissue to proliferate in the bulky structure of an absorbable multifilament draw-textured yarn according to claim 1.

5. The cell culture scaffold according to claim 4, wherein the absorbable multifilament draw-textured yarn comprises pores in the range of 1-150 μm in diameter.

6. An absorbable multifilament suture comprising an absorbable multifilament draw-textured yarn according to claim 1.

7. The absorbable multifilament suture according to claim 6, further comprising a surgical needle coupled with the absorbable multifilament draw-textured yarn.

8. The absorbable multifilament suture according to claim 6, wherein the absorbable multifilament draw-textured yarn comprises pores in the range of 1-150 μm in diameter.

9. An absorbable multifilament draw-textured yarn comprising an absorbable polymer,
wherein the absorbable multifilament draw-textured yarn includes a partial bulky structure having a bulkiness of 200-1000%,
wherein said partial bulky structure is a structure of the absorbable multifilament draw-textured yarn having pores between said filaments, said pores being greater than 1μm in diameter,
wherein said partial bulky structure comprises twisted or braided filaments,
wherein said bulkiness is a diameter ratio of a portion of the absorbable multifilament draw-textured yarn having a bulky structure relative to a portion of the absorbable multifilament yarn having no bulky structure.

* * * * *